United States Patent [19]

Gaskin

[11] Patent Number: 4,806,344

[45] Date of Patent: Feb. 21, 1989

[54] SUN PROTECTANT COMPOSITION AND METHOD

[76] Inventor: Frances C. Gaskin, 298 State St., Albany, N.Y. 12210

[21] Appl. No.: 635

[22] Filed: Jan. 5, 1987

[51] Int. Cl.$^4$ .......................... A61K 7/40; A61K 7/42; A61K 7/44; A61K 9/07
[52] U.S. Cl. ...................................... 424/59; 424/60; 514/937; 514/938; 514/939; 514/944; 514/969
[58] Field of Search .................................. 424/59, 60

[56] References Cited

U.S. PATENT DOCUMENTS

| 4,390,341 | 6/1983 | Jacobs | 424/60 |
| 4,419,343 | 12/1983 | Pauly | 424/59 |
| 4,453,941 | 6/1984 | Jacobs | 424/60 |
| 4,515,773 | 5/1987 | Herlihy | 424/59 |

OTHER PUBLICATIONS

Chemical Abstracts, 1972, vol. 76, p. 11127/c Johnson et al.
Chemical Abstracts, 1975, vol. 82, p. 64335p Sakamoto.
Christine Jaworsky, John L. Ratz and Jacob W. E. Dijkstra, "Efficacy of Tan Accelerators", *Journal of American Academy of Dermatology*, 1987; 16:769-771.
FDC Reports, Trademarks Reg. U.S. Patent Office, "The Rose Sheet", Apr. 13, 1987, vol. 8, No. 15, pp. 7 and 8.
Jean Seligmann, et al., "Catching Dangerous Rays", *Newsweek*, Jun. 24, 1985, p. 69.
Warwick L. Morison, "What is the Function of Melanin?", *Arch. Dermatol.*, vol. 121, Sep. 1985, pp. 1160-1163.
Letter to the Editor from Robert B. Armstrong, *Arch. Dermatol.*, vol. 122, Apr. 1986, pp. 373 and 374.
David M. Warshauer and John R. Steinbaugh, "Sunlight and Protection of the Skin", *AFP*, vol. 27, No. 6, Jun. 1983, pp. 109-115.
Lawrence E. Klein and James J. Nordlund, "Genetic Basis of Pigmentation and Its Disorders", reprinted from *International Journal of Dermatology*, Dec. 1981, vol. 20, No. 10, pp. 621-631.
Madhu A. Pathak and Dan L. Fanselow, "Photobiology of Melanin Pigmentation:Dose/Response of Skin to Sunlight and Its Contents", *Journal of American Academy of Dermatology*, 9:724-733, 1983.
Stephanie Russell, James B. Stafford and Richard F. Edlich, "Sunburn", *Current Concepts in Trauma Care*, Summer 1983, pp. 14-17.

Primary Examiner—Dale R. Ore
Attorney, Agent, or Firm—Hamilton, Brook, Smith & Reynolds

[57] ABSTRACT

The invention relates to a composition and method of dissolving melanin in a composition for the purpose of photoprotection of the human epidermis from exposure to the sun's harmful rays. The composition consists of melanin, as an active ingredient, sunscreens, vitamins and emollients. These ingredients are rapid blended by ultrasound for 2-3 hours to form a mixture that enhances the sun protective factor when applied topically.

36 Claims, No Drawings

SUN PROTECTANT COMPOSITION AND METHOD

BACKGROUND OF THE INVENTION

The sensitivity of the human skin to the ultraviolet rays (UVR) of the sun is determined by the amount of the pigment melanin contained within it. Many individuals with fair or light/white complexions (Skin Types I, II, III) burn because they do not produce sufficient melanin to protect the skin against sunburn. Moderately brown to darkskinned persons (Skin Types IV, V, VI) are not entirely protected from the deleterious effects of solar radiation. Skin Type I—always burns easily (freckles) and never tans; Skin Type II—always burns easily and tans minimally; Skin Type III—burns moderately and tans gradually; Skin Type IV—burns minimally and tans well; Skin Types V and VI—tan profusely but rarely burn.

In addition to sunburn, long-term exposure to the sun, particularly for individuals who do not produce sufficient melanin such as Skin Types I, II, III can lead to premature aging of the skin and cutaneous cancer, usually basal cell, squamous cell carcinomas and malignant melanomas. Darkskinned persons do develop skin cancer but in small percentages, for example, malignant melanomas may occur in areas of the body where melanin is least, such as the palmar surfaces of the hands and the plantar surface of the feet. Consequently, allergic reactions, coarseness, dryness, mottling, flaccidity and blemishes are also seen. To obviate these detrimental effects, experts in the field include various combinations and percentages of chemical, physical and natural sunscreens, with the sun protective factor (SPF) ranging from 2 to 30, that is, minimal sun protection to ultra sun protection. Further, melanin precursors—tyrosine, tyrosinase and 3,4 Dihydroxy Phenylalanine (DOPA) are included in suntan preparations to stimulate the production of melanin:

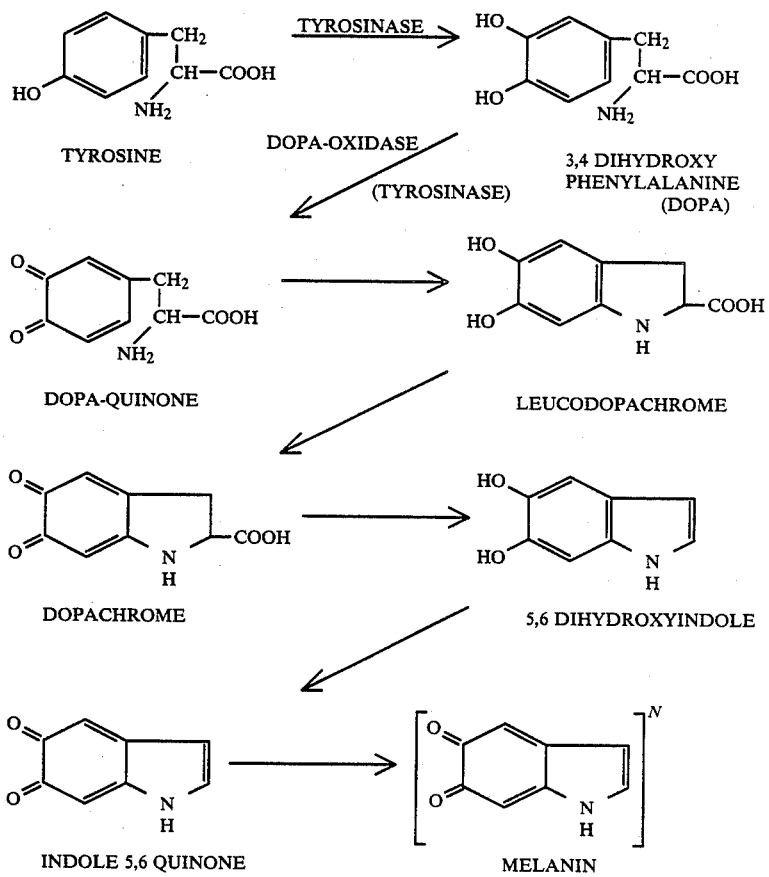

Yet, each year these harmful or life-threatening toxcities are increasingly becoming more widespread because the problem still exists for those persons who do not genetically possess sufficient melanocytes (pigment cells):

The pigment cell colors the skin by injecting melanosomes into keratinocytes. The keratinocyte carries its burden of pigment to the stratum corneum where it is shed as melanin dust. Melanin provides effective protection against actinic damage of the sun. Notably, there exists an increased correlation between skin sensitivity to UVR and melanin content. The degree of sunburn reaction, prevalence of abnormal photosensitivity and the degenerative (aging) and neoplastic changes are reduced with increasing melanin pigmentation. This increased relationship is correlated to the distribution of melansomes and quantity of melanin in the epidermis.

The SPF estimates of melanin have been cited as 1.0–4.3 to 5 for Skin Types I through Skin Types V and VI, respectively.

The photoprotective role of melanin is related to its physical and biochemical properties: melanin (a) scatters and degrades radiation to heat, (b) absorbs the radiation and promotes immediate oxidation reaction, and (c) quenches free radicals generated by UVR. Further, melanin in the human epidermis functions as a stable free radical. Because of its polyquinoid nature melanin acts as an electron exchange polymer and therefore is capable of undergoing an immediate photooxidation or darkening reaction. Melanin quenches the formulation of other types of damaging free radicals in the human epidermis upon exposure to UVR. This property of melanin to serve as a scavenger for damaging non-melanin free radicals may significantly contribute to its photo-protective role in individuals of Skin Types IV, V and VI.

However, the exposure to UVR itself, produces a phototherapeutic advantage. Subsequent to three exposures, the Type IV, V, VI skin become less likely to sunburn. However, Type I, II, III individuals develop very few melanized melanosomes. A melanin filter never develops in the stratum corneum resulting in an absence of melanin dust in the epidermis. Therefore, the need exists for the formulation of the topical application of melanin to protect the human skin from the UV rays of the sun.

BRIEF SUMMARY OF THE INVENTION

The subject invention provides a composition of ingredients which are non-mutagenic and non-allergic. These ingredients can be topically applied to the human skin to protect the skin from the damaging ultraviolet rays of the sun. More specifically, the subject invention concerns the use of an aliphatic compound, melanin, as well as vitamins, sunscreens and emollients. Heretofore, the state of the art has been to stimulate the production of melanin in the skin. But, in the absence of or deficiency of melanin in the epidermis, melanin can be applied directly to the skin. In the past, dissolving melanin in solution has presented a complex problem. However, in this subject invention, melanin is combined with ferric chloride and triethanolamine and rapid-blended by the ultrasound technique for 2-3 hours. This mixture and method, as well as other ingredients, are combined to make a suntan oil, creme and ointment that protect against the ultraviolet rays of the sun.

DETAILED DESCRIPTION OF THE INVENTION

As described above, melanin, the active ingredient, is mixed with triethanolamine and ferric chloride making a preparation of oil, creme and ointment to protect the skin from the ultraviolet rays of the sun. Appropriate ingredients are selected to form an oil, creme and ointment base from a group consisting of 1, 2, 3 trihydroxypropane, 4-para-aminobenzoic acid, 2-hydroxy-4-methoxylphenyl, 2-amino 3-p-hydroxyphenylpropanoic acid, hydroxyethane, 1-hexadecanol, 7-dehydrocholesterol, riboflavin, dimethylpolysiloxane, mineral oil, jojoba oil, mink oil and fragrance.

Typically these ingredients are present in concentrations of 0.5 ml to 20.0 ml and 1.0 mgm to 2.0 mgm. Individually, these ingredients may serve to penetrate the cellular structure of the epidermis, lubricate, screen or block as well as protect the skin from the harmful rays of the sun. Melanin is synthesized from tyrosinase and DOPA. Melanin 0.5 mgm, 1.0 mgm, 2.0 mgm is present in the final reaction mixture with a concentration of triethanolamine 10.0 cc, 10.0 cc, 10.0 cc and ferric chloride 1.0 mgm, 1.5 mgm, 2 mgm, respectively. The ingredients are rapid-blended with ultrasound for about 2-3 hours to break up and disperse the conglomerates. Further, substance can be added such as, beta carotene and petroleum to protect the skin from harmful ultraviolet rays. The value of the preparation can be enhanced by repeated applications of said composition to the skin before and during exposure to indoor solar simulators and outdoor sunlight.

The composition can be suspended in various cosmetic bases suitable for topical application to the human skin. For such application the base can take the forms of oil, creme and ointment, and the like. These ingredients can be used in varying concentrations, as discussed above, ranging from 0.5-20 ml and 0.5-2.0 mgm and can be used in various combinations to make a composition of the present invention. In particular, combinations of ingredients are used to prepare a sun protective factor up to 15 (SPF).

Thus, an oil can be prepared by methods well known in the art. Combine melanin 0.1 mgm to ferric chloride 0.1 mgm and triethanolamine 10.0 cc and rapid-blend the mixture by ultrasound for about 2 hours to break up and disperse the agglomerates. Add 0.1 mgm beta-carotene plus emollients, oil and vitamins to the base. Include sunscreens as mentioned above as desired to make a SPF up to 15.

EXAMPLE 1

A composition is prepared forming an oil with a sun protective factor of 2, comprising the following constituents:

| | |
|---|---|
| triethanolamine | 50.0 |
| diethylene glycol | 10.0 |
| ferric trichloride | 0.1 |
| melanin | 0.05 |
| riboflavin | 0.1 |
| beta-carotene | 0.1 |
| 1,2,3 trihydroxypropane | 27.0 |
| mink oil | 2.5 |
| jojoba oil | 2.5 |
| mineral oil | 0.25 |
| 4-para-aminobenzoic acid | 1.7 |
| dimethylpolysiloxane | 5.0 |
| fragrance | qs |
| Total | 100 |

A creme can be prepared by methods well known in the art. Combine melanin 1.0 mgm in ferric chloride 1.5 mgm and triethanolamine 10.0 cc and rapid-blend the mixture as described above here. Add 1.0 cc ethanol and 15.5 cc 1-hexadecanol. To this mixture add beta-carotene 1.5 mgm, vitamins and sunscreens, as mentioned above to reach the SPF of 15.

EXAMPLE 2

A composition is prepared forming a creme with a sun protective factor of 8, comprising the following constituents:

| | |
|---|---|
| triethanolamine | 27.0 |
| diethylene glycol | 5.5 |
| ferric trichloride | .27 |
| melanin | .002 |
| riboflavin | .27 |
| beta-carotene | .27 |
| 1,2,3 trihydroxypropane | 8.3 |
| 4-para-aminobenzoic acid | 6.0 |
| dimethylpolysiloxane | 5.5 |
| ethanol | 2.7 |
| 1-hexadecanol | 43.0 |
| water | qs |
| fragrance | qs |

An ointment can be prepared by methods well known in the art. Combine melanin 1.5 mgm to ferric chloride 2.0 mgm and triethanolamine 10.0 cc and rapid-blend the mixture by ultrasound for about 3 hours to break up and disperse the conglomerates. Add 20.0 cc of petrolatum and beta-carotene 2.0 mgm plus emollients and vitamins to the base. Include sunscreens as mentioned above as desired to make an SPF up to 15.

EXAMPLE 3

A composition is prepared forming an ointment with a sun protective factor of 15.

| | |
|---|---|
| triethanolamine | 21.0 |
| diethylene glycol | 4.0 |
| ferric trichloride | 0.2 |
| melanin | .09 |
| riboflavin | .2 |
| beta-carotene | .2 |
| 1,2,3 trihydroxypropane | 5.0 |
| 4-para-aminobenzoic acid | 14.0 |
| dimethylpolysiloxane | 6.0 |
| petrolatum | 43.0 |
| 2-hydroxy-4-methoxylphenyl | 6.0 |
| fragrance | qs |
| Total | 100 |

Sunscreening agents considered safe and effective by the Federal Drug Administrations may be included. These sunscreens and dose limits by percentages are listed as follows: glyceryl aminobenzoate 3.0–5.0; amyl p-dimethylamino benzoate (Padimate A) 1.0–5.0; 2-ehtylhexyl-p-dimethylamino benzoate (Padimate O) 1.4–8.0; 2-ethoxy-ethylhexyl-p-methoxy cinnamate (cinnoxate) 1.0–3.0; diethanolamine-p-methoxycinnamate 8.0–10.0; ethylhexyl-p-methoxycinnamate 2.0–7.5; 2,2-dihydroxy-4-methoxybenzophenone (dioxybenzone) 3.0; 2-hydroxy-r-methoxybenzophenone-5 sulfonic acid (sulisobenzone) 5.0–10.0; 2-ethyl-hexyl-2-cyano-3, 3-diphenylacrylate 7.0–10.0; ethyl-4-bis-(hydroxypropyl-)-amino benzoate 1.0–5.0; ethyl-4-bis-(hydroxypropyl-)-amino benzoate 1.0–5.0; digalloyl thioleate 1.0–5.0; 2-ethylhexylsalicylate 3.0–5.0; lawsome+dihydroxyacetone 0.25–3.0; 3,3,5-trimethylcyclohexyl salicylate (homosalate) 4.0–15.0; methylanthranilate 3.5–4.0; 2-phenyl-benzimidazole-5 sulfonic acid 1.0–4.0; triethanolamine salicylate 5.0–12.0; red veterinary petrolatum 30.0–100; titanium dioxide 2.0–25.0. Each one of these sunscreens in varying percentages operate to filter out the harmful ultraviolet rays of the sun.

It should be comprehended that the cosmetic base in oil, creme or ointment form, can be differently combined in accordance with those experts knowledgeable in the art to provide a suitable carrier for the melanin-based product. The examples written above here about the subject invention can be varied by those skilled in the art without departing from the fundamentals of the subject invention. Thus, it can be seen that the subject invention may be produced through the process of the present invention. The composition and method herein employ compositions of ingredients which may be safely used on the skin. The invention may be used in the form of oil, creme and ointment. The description herein is therefore considered in all respects as illustrative and limited in breadth and scope of the invention being indicated by the subsequent claims rather than by the foregoing description.

What is claimed is:

1. A composition for protecting the skin against ultraviolet rays, comprising:
   a cosmetic base in the form of an oil, cream or ointment;
   effective amounts of melanin, ferric chloride and triethanolamine; and
   at least one sunscreen singly or in combination to provide up to 15 sun protective factor.

2. A composition according to claim 1 wherein said melanin is present at a concentration of 0.05 mgm percent to 0.09 mgm percent.

3. A composition according to claim 1 wherein said ferric chloride is present at a concentration of 0.09 mgm percent to 0.1 mgm percent.

4. A composition according to claim 1 wherein said triethanolamine is present at a concentration of 21%–50%.

5. A composition as claimed in claim 1 further comprising fragrance.

6. A composition as claimed in claim 1 further comprising a vitamin.

7. A composition as claimed in claim 1 further comprising beta-carotene.

8. A composition as claimed in claim 1 wherein at least one sunscreen is selected from the group consisting of 4-para-aminobenzoic acid, petrolatum and mink oil.

9. A composition as claimed in claim 1 wherein the cosmetic base includes at least one ingredient selected from the group consisting of 1, 2, 3 trihydroxypropane, 2-hydroxy-4-methoxylphenyl, hydroxyethane, 1-hexadecanol, 7-dehydrocholesterol, water, dimethylpolysiloxane, mineral oil and jojoba oil.

10. A composition as claimed in claim 1 further comprising riboflavin.

11. A composition for topical application to the skin to protect the skin against ultraviolet rays, the composition comprising:
   an effective amount of melanin combined with triethanolamine and ferric chloride; and
   a cosmetic base suitable for topical application to the skin in which the melanin reacted with ferric chloride and triethanolamine is distributed.

12. A composition as claimed in claim 11 wherein the base suitable for topical application is a cosmetic base in the form of an oil, cream or ointment.

13. A composition as claimed in claim 11 wherein the vehicle for topical application comprises an effective amount of at least one ingredient selected from the group consisting of beta-carotene, 1, 2, 3 trihydroxypropane, 4-para-aminobenzoic acid, 2-hydroxy-4-methoxylphenyl, hydroxyethane, 1-hexadecanol, 7-dehydrocholesterol, riboflavin, water, dimethylpolysiloxane, petrolatum, mineral oil, jojoba oil, mink oil, and fragrance.

14. A composition as claimed in claim 11 wherein said ferric chloride is present at a concentration of from about 0.1 percent to about 0.27 percent.

15. A composition as claimed in claim 11 wherein said melanin is present at a concentration of from about 0.002 percent to about 0.09 percent.

16. A composition as claimed in claim 11 wherein said triethanolamine is present at a concentration of from about 21 percent to about 50 percent.

17. A composition as claimed in claim 11 further comprising sufficient amounts of a sunscreen, singly or in combination, to produce a composition having a sun protective factor of up to 15.

18. A composition for topical application to the skin to protect the skin against ultraviolet rays comprising:
   a cosmetic base in the form of an oil, cream or ointment; and
   effective amounts of melanin, ferric chloride and triethanolamine.

19. A composition as claimed in claim 18 wherein the melanin is present at a concentration of from about 0.002 percent to about 0.09 percent.

20. A composition as claimed in claim 18 wherein the triethanolamine is present at a concentration of about 20 percent to about 50 percent.

21. A composition as claimed in claim 18 further comprising beta-carotene.

22. A composition as claimed in claim 18 wherein the ferric chloride is present at a concentration of about 0.1 percent to about 0.27 percent.

23. A composition as claimed in claim 18 further comprising a sunscreen.

24. A composition for topical application to the skin to protect the skin against ultraviolet rays comprising:
   an effective amount of melanin combined with an effective amount of triethanolamine;
   an effective of ferric chloride;
   and further comprising beta-carotene;
   4-para-aminobenzoic acid;
   diethylene glycol;
   1, 2, 3 trihydroxypropane;
   dimethylpolysiloxane; and
   riboflavin.

25. A composition as claimed in claim 24 further comprising mink oil, jojoba oil and mineral oil.

26. A composition as claimed in claim 24 further comprising ethanol, water and 1-hexadecanol.

27. A composition as claimed in claim 24 further comprising petrolatum and 2-hydroxy-4-methoxylphenyl.

28. A method of making a composition for topical application to human skin to protect the skin against ultraviolet rays or rays of the sun, the method comprising the steps of:
   blending an effective amount of melanin with effective amounts of triethanolamine and ferric chloride; and
   distributing the mixture in a cosmetic base suitable for topical application to the skin.

29. A method as claimed in claim 28 wherein the step of blending includes rapid blending by ultrasound.

30. A method as claimed in claim 28 wherein said ferric chloride is present at a concentration in the range of about 0.1 percent to about 0.27 percent.

31. A method as claimed in claim 28 wherein the melanin is present at a concentration in the range of about 0.002 percent to about 0.09 percent.

32. A method as claimed in claim 28 wherein said triethanolamine is present at a concentration in the range of about 21 percent to about 50 percent.

33. A method as claimed in claim 28 wherein the cosmetic base has a form of an oil, cream or ointment and comprises ingredients selected from the group consisting of beta-carotene, 1, 2, 3 trihydroxypropane, 4-para-aminobenzoic acid, 2-hydroxy-4-methoxylphenyl, hydroxyethane, 1-hexadecanol, 7-dehydrocholesterol, riboflavin, water, dimethylpolysiloxane, petrolatum, mineral oil, jojoba oil, mink oil, and fragrance.

34. A method as claimed in claim 28 further comprising the step of adding at least one sunscreen singularly or in combination to the skin protectant composition to produce a composition of sun protective factor up to 15.

35. A method of protecting human skin against ultraviolet rays comprising the step of:
   topically applying to the skin a composition for protecting the skin against ultraviolet rays an having an effective amount of melanin as an active ingredient combined with ferric chloride and triethanolamine.

36. A method as claimed in claim 35 wherein the melanin is combined with ferric chloride and triethanolamine is distributed in a cosmetic base suitable for topical application to the skin such that the topical application of the composition to the skin provides protection against ultraviolet rays.

* * * * *